(12) United States Patent
Hibner et al.

(10) Patent No.: US 9,538,994 B2
(45) Date of Patent: *Jan. 10, 2017

(54) VACUUM SENSOR AND PRESSURE PUMP FOR TETHERLESS BIOPSY DEVICE

(75) Inventors: John A. Hibner, Mason, OH (US); William D. Dannaher, Cincinnati, OH (US); Wells D. Haberstich, Loveland, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 445 days.

This patent is subject to a terminal disclaimer.

(21) Appl. No.: 13/247,495

(22) Filed: Sep. 28, 2011

(65) Prior Publication Data

US 2012/0016262 A1    Jan. 19, 2012

Related U.S. Application Data

(63) Continuation of application No. 11/965,048, filed on Dec. 27, 2007, now Pat. No. 8,057,402.

(51) Int. Cl.
*A61B 10/00* (2006.01)
*A61B 10/02* (2006.01)
*A61B 17/00* (2006.01)

(52) U.S. Cl.
CPC ........ *A61B 10/0275* (2013.01); *A61B 10/0283* (2013.01); *A61B 2010/0208* (2013.01); *A61B 2017/00398* (2013.01)

(58) Field of Classification Search
CPC ................................................. A61B 10/0275
(Continued)

(56) References Cited

U.S. PATENT DOCUMENTS

| 5,526,822 A | 6/1996 | Burbank et al. |
| 6,086,544 A | 7/2000 | Hibner et al. |

(Continued)

FOREIGN PATENT DOCUMENTS

| AU | 2008255246 | 7/2009 |
| CA | 2647269 | 6/2009 |

(Continued)

OTHER PUBLICATIONS

Partial Search Report dated Apr. 14, 2010 for Application No. EP 08254141.8.

(Continued)

*Primary Examiner* — Joseph Stoklosa
(74) *Attorney, Agent, or Firm* — Frost Brown Todd LLC (57) ABSTRACT

A biopsy device may include a needle, a cutter, and a handpiece. A vacuum pump in the handpiece may provide a vacuum to the needle and/or to the cutter. A pressure pump in the handpiece may also provide pressurized air to the needle and/or to the cutter. A motor in the handpiece may drive the vacuum pump, the pressure pump, and/or the cutter. A vacuum sensor may sense a vacuum level within the biopsy device, and cause initiation of operational cycles in response to sensed vacuum levels. Portions of a valving mechanism and a clutching mechanism may be integrally formed. A clutching and valving mechanism may be driven by a first battery-powered motor; and a cutter, pressure pump, and vacuum pump by a second battery-powered motor. A biopsy device may thus provide vacuum, pressurized air, and power from within a handpiece, such that the biopsy device is tetherless.

13 Claims, 9 Drawing Sheets

(58) Field of Classification Search
USPC .................... 600/562, 564–566, 568
See application file for complete search history.

(56) References Cited

U.S. PATENT DOCUMENTS

| | | | |
|---|---|---|---|
| 6,231,522 B1 | 5/2001 | Voegele et al. | |
| 6,485,436 B1 | 11/2002 | Truckai et al. | |
| 6,626,849 B2 | 9/2003 | Hitema et al. | |
| 7,442,171 B2 | 10/2008 | Stephens et al. | |
| 7,517,321 B2 | 4/2009 | McCullough et al. | |
| 7,662,109 B2 | 2/2010 | Hibner | |
| 7,828,748 B2 | 11/2010 | Hibner | |
| 7,854,706 B2 | 12/2010 | Hibner | |
| 7,918,804 B2 | 4/2011 | Monson et al. | |
| 7,938,786 B2 | 5/2011 | Ritchie et al. | |
| 8,016,772 B2 | 9/2011 | Heske et al. | |
| 8,057,402 B2 * | 11/2011 | Hibner et al. | 600/566 |
| 2004/0249307 A1 * | 12/2004 | Thompson et al. | 600/568 |
| 2005/0113715 A1 | 5/2005 | Schwindt | |
| 2006/0173377 A1 * | 8/2006 | McCullough et al. | 600/566 |
| 2008/0195066 A1 | 8/2008 | Speeg et al. | |
| 2012/0016262 A1 * | 1/2012 | Hibner et al. | 600/566 |

FOREIGN PATENT DOCUMENTS

| | | |
|---|---|---|
| CN | 101011270 A | 8/2007 |
| CN | 101502427 | 8/2009 |
| CN | 102641140 B | 5/2015 |
| EP | 1 815 798 | 8/2007 |
| EP | 2074950 B1 | 10/2011 |
| EP | 2412314 A2 | 2/2012 |

OTHER PUBLICATIONS

U.S. Appl. No. 60/869,736, filed Dec. 13, 2006, Ritchie.
U.S. Appl. No. 60/874,792, filed Dec. 13, 2006, Hibner et al.
Australian Patent Examination Report No. 1, dated Jan. 17, 2013, for Application No. AU 2008255246, 3 pgs.
Chinese Office Action, No. 1, dated Dec. 13, 2011, for Application No. CN 200810185010.1, 14 pgs.
Chinese Office Action, No. 2, dated Aug. 30, 2012, for Application No. CN 200810185010.1, 6 pgs.
Chinese Office Action, No. 1, dated Dec. 3, 2013, for Application No. CN 201210094039.5, 9 pgs.
Chinese Office Action, No. 2, dated Sep. 15, 2014, for Application No. CN 201210094039.5, 8 pgs.
Extended European Search Report and Written Opinion with European Communication dated Aug. 20, 2010, for Application No. EP 08254141.8, 11 pgs.
European Search Report and Written Opinion dated Jan. 12, 2012 for Application No. EP 11185873, 6 pgs.
European Communication dated Dec. 11, 2012 for Application No. EP 11185873.4, 5 pgs.
European Communication dated Nov. 6, 2015 for Application No. EP 11185873.4, 4 pgs.
Canadian Office Action dated Jun. 21, 2016 for Application No. 2,647,269, 4 pages.
Australian Office Action dated Oct. 8, 2016 for Application No. 2015271895, 3 pages.

* cited by examiner

VACUUM SENSOR AND PRESSURE PUMP FOR TETHERLESS BIOPSY DEVICE

PRIORITY

The present application is a continuation of U.S. patent application Ser. No. 11/965,048, entitled "Vacuum Sensor and Pressure Pump for Tetherless Biopsy Device," filed Dec. 27, 2007, the disclosure of which is hereby incorporated by reference in its entirety.

BACKGROUND

Biopsy samples have been obtained in a variety of ways in various medical procedures using a variety of devices. Biopsy devices may be used under stereotactic guidance, ultrasound guidance, MRI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2007/0118048, entitled "Remote Thumbwheel for a Surgical Biopsy Device," published May 24, 2007; U.S. Provisional Patent Application Ser. No. 60/869,736, entitled "Biopsy System," filed Dec. 13, 2006; U.S. Provisional Patent Application Ser. No. 60/874,792, entitled "Biopsy Sample Storage," filed Dec. 13, 2006; and U.S. Non-Provisional patent application Ser. No. 11/942,764, entitled "Vacuum Timing Algorithm for Biopsy Device," filed Nov. 20, 2007. The disclosure of each of the above-cited U.S. patents, U.S. patent application Publications, U.S. Provisional patent applications, and U.S. Non-Provisional patent application is incorporated by reference herein.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
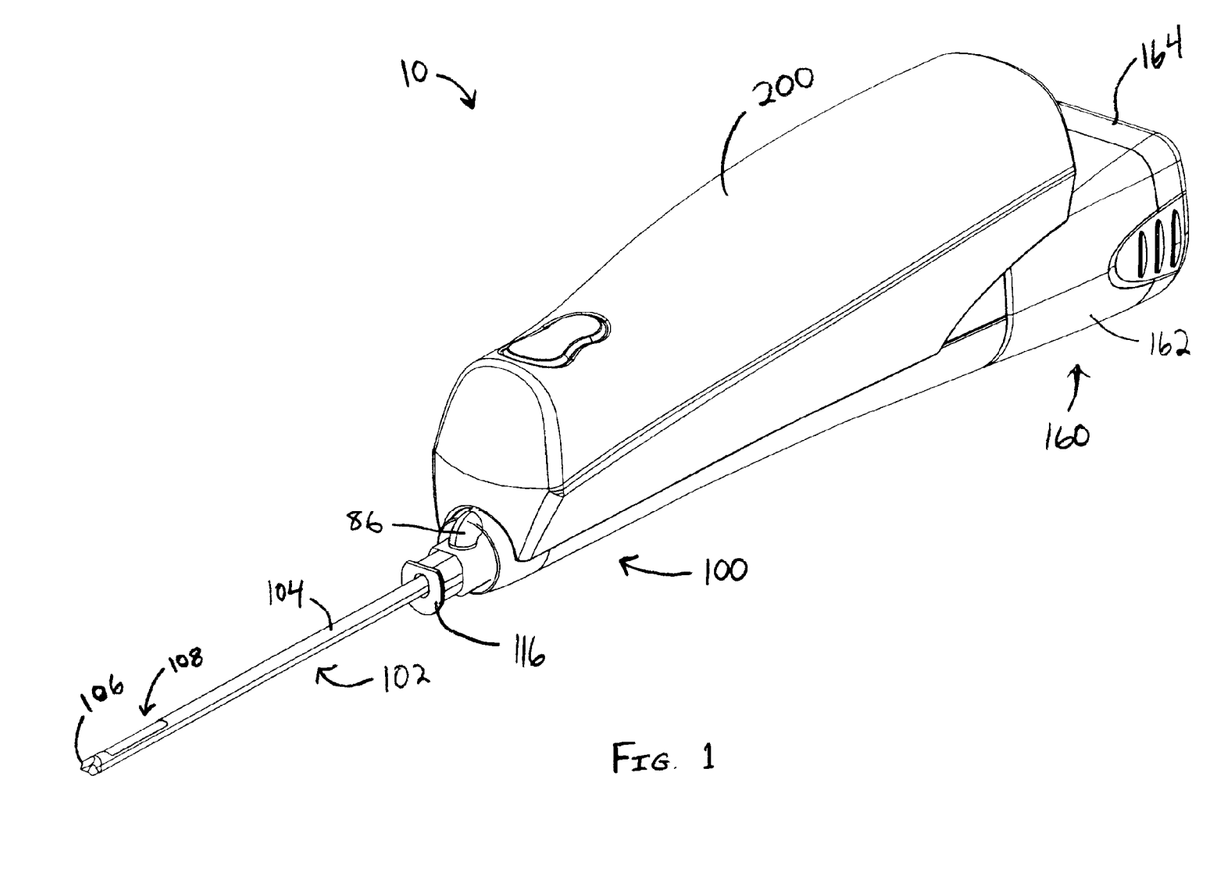
FIG. 1 depicts a perspective view of an exemplary tetherless biopsy device.

As shown in FIG. 1, an exemplary biopsy device (10) comprises a probe (100) and a holster (200). In some embodiments, probe (100) is separable from holster (200). By way of example only, probe (100) may be provided as a disposable component, while holster (200) may be provided as a reusable component.

Use of the term "holster" herein should not be read as necessarily requiring any portion of probe (100) to be inserted into any portion of holster (200). Indeed, in some variations of biopsy device (10), probe (100) may simply sit on holster (200) (e.g., holster (200) acts like a "cradle," etc.), or holster (200) may simply sit on probe (100). In some other variations, a portion of holster (200) may be inserted into probe (100). In either such variations, probe (100) may be secured relative to holster (200) using any suitable structures or techniques (e.g., clips, clasps, snap-fit components, etc.). Furthermore, in some biopsy devices (10), probe (100) and holster (200) may be of unitary or integral construction, such that the two components cannot be separated or are not formed separately. Still other suitable structural and functional relationships between probe (100) and holster (200) will be apparent to those of ordinary skill in the art in view of the teachings herein.

Biopsy device (10) of the present example is configured to be handheld, such that biopsy device (10) may be manipulated and operated by a single hand of a user (e.g., using ultrasound guidance, etc.). However, it will be appreciated in view of the disclosure herein that biopsy device (10) may be used in a variety of other settings (e.g., stereotactic, MRI, etc.) and in other combinations.

In the present example, probe (100) comprises a needle portion (102) and a tissue sample holder (160). Needle portion (102) terminates in a hub (116). Needle portion (102) comprises an outer cannula (104) having a tissue piercing tip (106) and a transverse tissue receiving aperture (108) located proximally from the tissue piercing tip (106). Tissue piercing tip (106) is configured to penetrate tissue without requiring a high amount of force, and without requiring an opening to be preformed in the tissue prior to insertion of tip (106). Suitable configurations for tissue piercing tip (106) will be apparent to those of ordinary skill in the art in view of the teachings herein.

Figure 4:
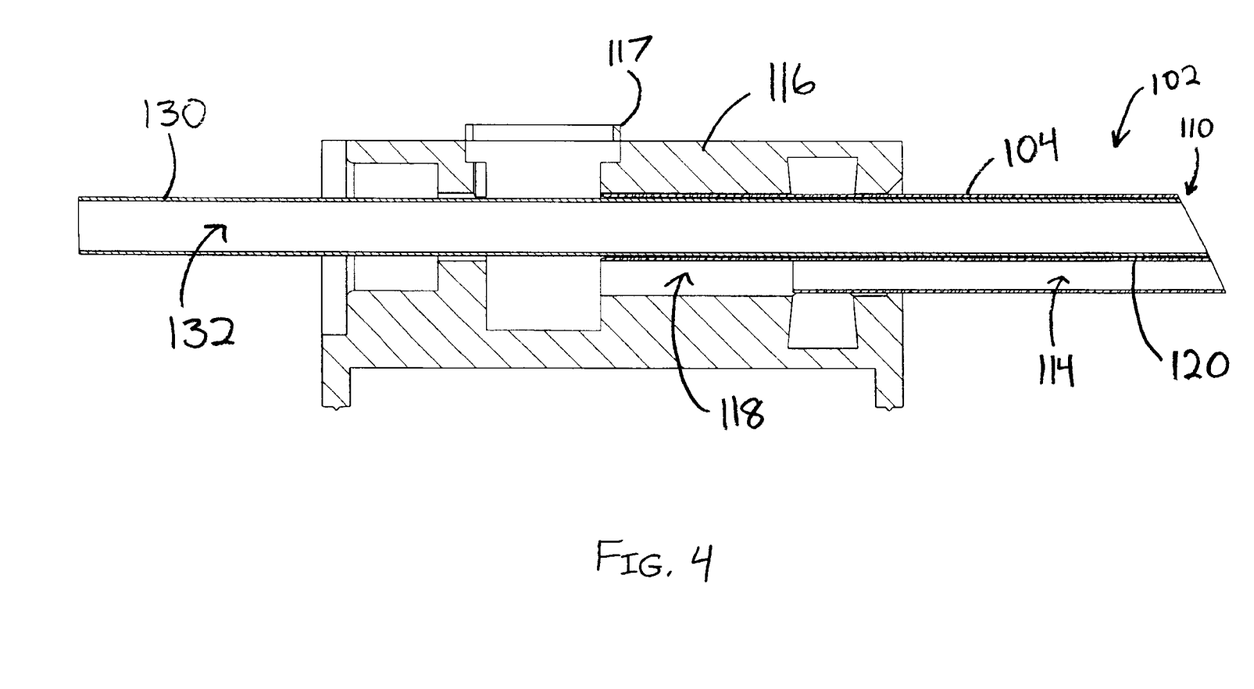
FIG. 4 depicts a cross-sectional view of an exemplary needle hub of the biopsy device of FIG. 1.

As shown in FIG. 4, the interior of outer cannula (104) of the present example defines a cannula lumen (110) and a vacuum lumen (114), with a wall (120) separating the cannula lumen (110) from the vacuum lumen (114). A plurality of external openings (not shown) are formed in outer cannula (104), and are in fluid communication with vacuum lumen (114). Examples of such external openings are disclosed in U.S. Pub. No. 2007/0032742, entitled "Biopsy Device with Vacuum Assisted Bleeding Control," published Feb. 8, 2007, the disclosure of which is incorporated by reference herein. Of course, as with other components described herein, such external openings are merely optional.

In some embodiments, wall (120) extends a substantial amount of the length of needle portion (112). In other embodiments, wall (120) proximally extends just past the region where the distal end of a cutter (130), which will be described below, terminates in needle portion (102). For instance, cannula lumen (110) may be sized and configured such that, with cutter (130) disposed therein, a gap exists between the exterior of cutter (130) and at least a portion of the interior of cannula (104). Such a gap may provide a vacuum lumen (114) along the length of cannula (104) proximal to the proximal end of wall (120). Still other ways in which a vacuum lumen (114) may be provided will be apparent to those of ordinary skill in the art in view of the teachings herein.

In the present example, a plurality of transverse openings (not shown) are formed through wall (120) to provide fluid communication between cannula lumen (110) and vacuum lumen (114). Suitable transverse openings are known in the art. The transverse openings in this example are located directly below aperture (108), though one or more of such openings may be located distally or proximally relative to aperture (108). As will be described in greater detail below, vacuum, saline, atmospheric air, and/or pressurized air may be communicated from vacuum lumen (114) to cannula lumen (110) via such transverse openings.

A hollow cutter (130) is disposed within cannula lumen (110). The interior of cutter (130) defines a cutter lumen (132), such that fluid and tissue may be communicated through cutter (130) via cutter lumen (132). As will be described in greater detail below, cutter (130) is configured to rotate within cannula lumen (110) and translate axially within cannula lumen (110). In particular, cutter (130) is configured to sever a biopsy sample from tissue protruding through transverse aperture (108) of outer cannula (104). As will also be described in greater detail below, cutter (130) is further configured to permit severed tissue samples to be communicated proximally through cutter lumen (132). Merely illustrative examples of such severing and proximal communication are described in U.S. Pat. No. 5,526,822, the disclosure of which is incorporated by reference herein, though any other suitable structures or techniques may be used for severing and/or communicating tissue samples within a biopsy system.

In the present example, the axial position of needle portion (102) is substantially fixed relative to the remainder of biopsy device (10). However, other variations may include a needle portion (102) that is axially translatable relative to at least a portion of the remainder of biopsy device (10). For instance, a biopsy device (10) may include a firing mechanism (not shown) that is operable to fire needle portion (102) into tissue. Such a firing mechanism may be spring driven and/or motor driven and/or otherwise driven.

In addition, the angular position of needle portion (102) in the present example is substantially fixed relative to the remainder of biopsy device (10). However, other variations may include a needle portion (102) that is rotatable relative to at least a portion of the remainder of biopsy device (10). For instance, a biopsy device (10) may include a needle rotation mechanism (not shown) that is operable to rotate needle portion (102). Such a needle rotation mechanism may be thumbwheel driven and/or motor driven and/or otherwise driven. Similarly, a thumbwheel may be provided near the interface of needle portion (102) and probe (100), such as at a needle hub (116), for rotation of needle portion (102). Other ways of providing translation and/or rotation of needle portion (102) will be apparent to those of ordinary skill in the art.

Tissue sample holder (160) of the present example is configured to collect tissue samples communicated proximally through cutter lumen (132). In addition, at least a portion of tissue sample holder (160) is removable from probe (100), though tissue sample holder (160) may be non-removable in other versions. In some versions, tissue sample holder (160) comprises a manifold (not shown) that is configured to provide re-directed fluid communication between components of biopsy device (10). For instance, a manifold may re-direct fluid, such as a vacuum, communicated from a vacuum pump (e.g., from vacuum pump (80), described in further detail below) to cutter lumen (132) and/or elsewhere.

In addition, a manifold or other component of tissue sample holder (160) may be rotatable relative to at least some other portion of probe (100). For instance, a manifold or other component of tissue sample holder (160) may include a plurality of tissue sample compartments (not shown), and the manifold or other component of tissue sample holder (160) may be rotatable to successively index each of the tissue sample compartments with cutter lumen (132) to successively capture a discrete tissue sample in each tissue sample compartment. Such rotatability may be provided automatically (e.g., via a motor) and/or manually (e.g., by a user manually rotating a component of tissue sample holder (160), such as a knob). Alternatively, tissue sample holder (160) may be configured such that other components or no components thereof are rotatable.

Tissue sample holder (160) may further comprise an outer cup (162) or other component that is configured to provide a seal for the contents of tissue sample holder (160). Such a cup (162) may be substantially transparent and/or translucent to permit a user to view tissue samples and/or liquid, etc. within tissue sample holder (160). In addition, a tissue sample holder (160) may include trays or strips (not shown) that are removable therefrom. For instance, such trays or strips may define tissue sample compartments, and tissue samples may be removed from tissue sample holder (160) by removing the trays or strips. Such trays or strips may also permit fluid to be communicated therethrough, such that the trays or strips do not obstruct a fluid path between a manifold and cutter lumen (132). Of course, a cup and/or trays or strips may be provided in a variety of alternative ways, or may be omitted altogether.

In still other embodiments, tissue sample holder (160) simply comprises a chamber, without a rotatable manifold or similar components. For instance, tissue sample holder (160) may provide a reservoir-like configuration, and may hold materials such as tissue samples and liquids (e.g., blood, saline, etc.) together. In some variations, a screen, filter, or other structure is provided to facilitate separation of solids from liquids. In addition, one or more filters or other components may be provided to prevent liquids, tissue, etc. from entering vacuum pump (80), which will be described in greater detail below.

Tissue sample holder (160) of the present example comprises a cap (164), which can be removed from cup (162) to access tissue samples within cup (162). The interface between cup (162) and cap (164) may be substantially fluid tight. Other suitable features for cap (164) will be apparent to those of ordinary skill in the art in view of the teachings herein. Alternatively, cap (164) may be omitted.

By way of example only, suitable components for, configurations of, and methods of operating a tissue sample holder (160) are disclosed in U.S. Provisional Patent Application Ser. No. 60/874,792, entitled "Biopsy Sample Storage," filed Dec. 13, 2006; and U.S. Non-Provisional patent application Ser. No. 11/942,785, entitled "Revolving Tissue Sample Holder for Biopsy Device," filed Nov. 20, 2007. The disclosure of each of the above-cited U.S. patents, U.S. patent application Publications, U.S. Provisional patent applications, and U.S. Non-Provisional patent application is incorporated by reference herein. Still other suitable components for, configurations of, and methods of operating a tissue sample holder (160) will be apparent to those of ordinary skill in the art in view of the teachings herein.

As shown in FIGS. 2-3 and 7-8, a valve manifold (12) and valving member (20) are provided at the proximal end of needle portion (102). Valve manifold (12) of this example comprises three ports (14, 16, 18), each of which is in fluid communication with the interior of valve manifold (12). Port (14) is fluidly coupled with a conduit (82), which is also fluidly coupled with vacuum pump (80) via tissue sample holder (160) as described in further detail below. Conduit (82) and port (14) thus provide fluid communication between the interior of valve manifold (12) and vacuum pump (80).

Port (16) of the present example is fluidly coupled with a conduit (92), which is also fluidly coupled with a pressure pump (90) as described in further detail below. Conduit (92) and port (16) thus provide fluid communication between the interior of valve manifold (12) and pressure pump (90).

Port (18) is fluidly coupled with a conduit (86), which is also fluidly coupled with a port (117) of needle hub (116). Conduit (86) and ports (18, 117) thus provide fluid communication between the interior of valve manifold (12) and needle hub (116). In addition, as shown in FIG. 4, needle hub (116) of the present example defines an internal conduit (118), which is in fluid communication with port (117) and with vacuum lumen (114) of needle portion (102). Internal conduit (118) is also in fluid communication with conduit (86) via port (117). Accordingly, the interior of valve manifold (12) may be in fluid communication with vacuum lumen (114) via ports (18, 117), conduit (86), and internal conduit (118) of needle hub (116). In other embodiments, valve manifold (12) is unitarily integral with needle hub (116), such that ports (18, 117) and conduit (86) are not included. Still other ways in which a valve manifold (12) and a vacuum lumen (114) may be placed in fluid communication will be apparent to those of ordinary skill in the art in view of the teachings herein.

While port (14) of the present example is used for providing a vacuum; and port (16) for providing pressurized air, it will be appreciated that either port (14, 16) may be used to provide any other desired fluid communication (e.g., saline, vacuum, atmospheric air, etc.). Furthermore, either or both port (14, 16) may be omitted, or additional ports may be added.

As will be described in greater detail below, valving member (20) is configured to selectively provide communication between port (18) and a selected one of ports (14, 16), via the interior of manifold (12). In other words, in the present example, valving member (20) is configured to selectively communicate a vacuum from port (14) to port (18), or atmospheric air from port (16) to port (18), and therefore to vacuum lumen (114).

As shown in FIGS. 2-3 and 7-8, a portion of valving member (20) of the present example is disposed within valve manifold (12). Valving member (20) is also configured to longitudinally translate within valve manifold (12) and relative to needle portion (102). In particular, the longitudinal position of valve manifold (12) and needle portion (102) are fixed relative to probe (100) in this example. Valve member (20) also includes a plurality of annular seals (38). Seals (38) are configured to provide sealing engagement with valve manifold (12), such that seals (38) prevent fluid (e.g., liquid, vacuum, atmospheric air, pressurized air, etc.) from passing between seals (38) and the interior wall of valve manifold (12). Seals (38) may comprise a rubber and/or other suitable material(s).

Figure 7:
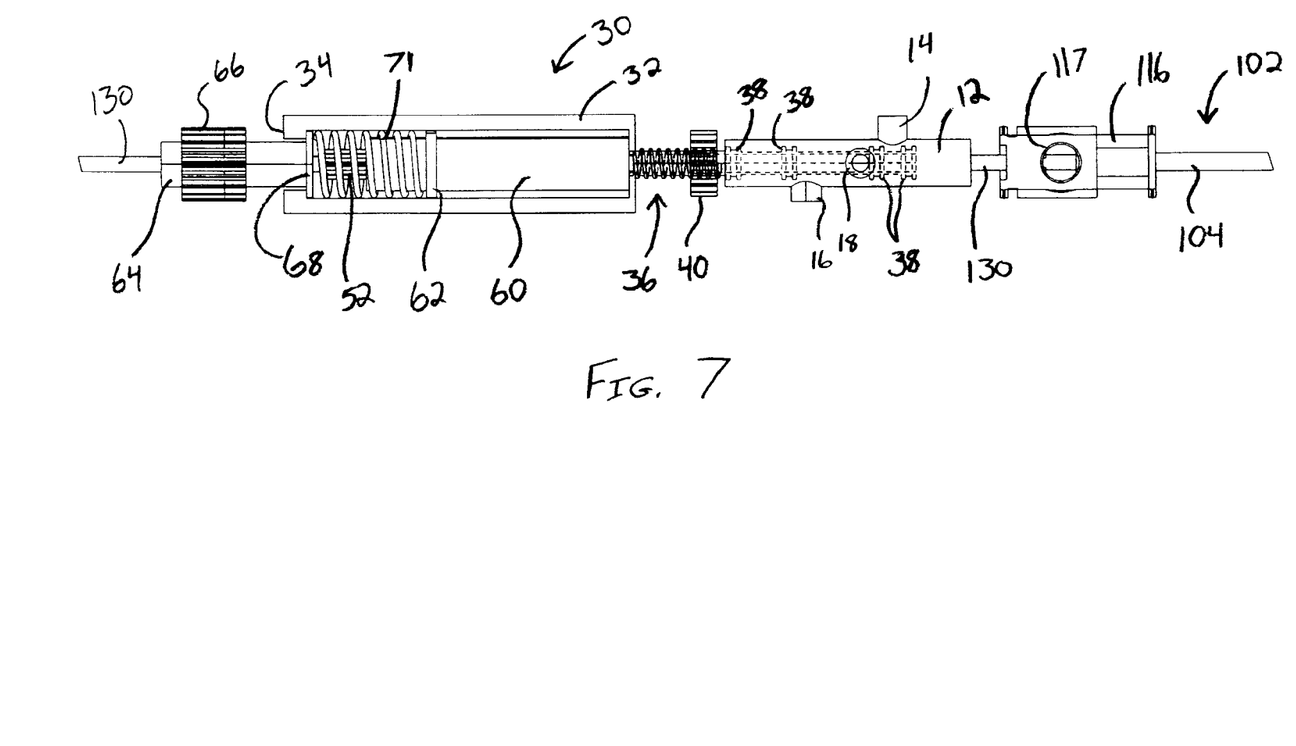
FIG. 7 depicts an exemplary clutching and valving mechanism with the fork member of FIG. 5 in a proximal position.

As described in greater detail below, and with reference to FIGS. 7-8, the longitudinal position of valving member (20) provides selective communication between ports (14, 16, 18). In particular, FIG. 7 shows valving member (20) in a proximal position. In this position, seals (38) provide fluid isolation of port (14). In other words, fluid communicated to port (14) will not pass beyond seals (38) when valving member (20) is in a proximal position in the present example. However, with valving member (20) in a proximal position as shown in FIG. 7, seals (38) permit fluid communication between port (16) and port (18). In particular, with port (16) receiving pressurized air generated by pressure pump (90) via conduit (92), such pressurized air will also be communicated to port (18) through valve manifold (12). With port (18) being in fluid communication with vacuum lumen (114) of needle portion (102) as described above, pressurized air will be further communicated to vacuum lumen (114) through port (16) when valving member (20) is in a proximal position as shown in FIG. 7 in the present example.

Figure 8:
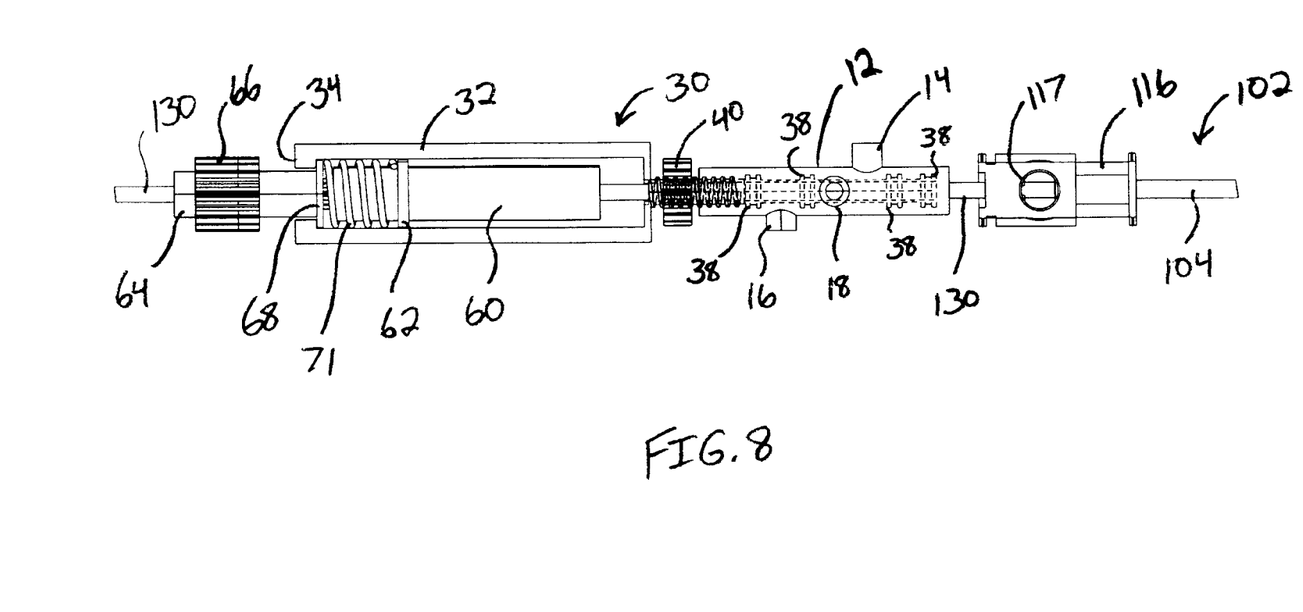
FIG. 8 depicts an exemplary clutching and valving mechanism with the fork member of FIG. 5 in a distal position.

FIG. 8 shows valving member (20) in a distal position. In this position, seals (38) provide fluid isolation of port (16). In other words, pressurized air communicated to port (16) will not pass beyond seals (38) when valving member (20) is in a distal position in the present example. However, with valving member (20) in a distal position as shown in FIG. 8, seals (38) permit fluid communication between port (14) and port (18). In particular, when vacuum that is induced using vacuum pump (80) is communicated to port (14) via conduit (82), such a vacuum will also be communicated to port (18) through valve manifold (12). With port (18) being in fluid communication with vacuum lumen (114) of needle portion (102) as described above, vacuum will be communicated to vacuum lumen (114) through port (14) when valving member (20) is in a distal position as shown in FIG. 8 in the present example.

Of course, valving member (20), valve manifold (12), ports (14, 16, 18), and seals (38) are merely one example of how vacuum lumen (114) may be selectively placed in communication with a vacuum or pressurized air. It will be appreciated in view of the teachings herein that a variety of alternative structures, mechanisms, and techniques may be used to selectively vary fluid communication to a vacuum lumen (114). Furthermore, while structures will be described below for selectively moving valving member (20) proximally and distally to change the relationship between valving member (20) and valve manifold (12), various other structures, mechanisms, and techniques for providing the same will be apparent to those of ordinary skill in the art in view of the teachings herein.

Figure 6:
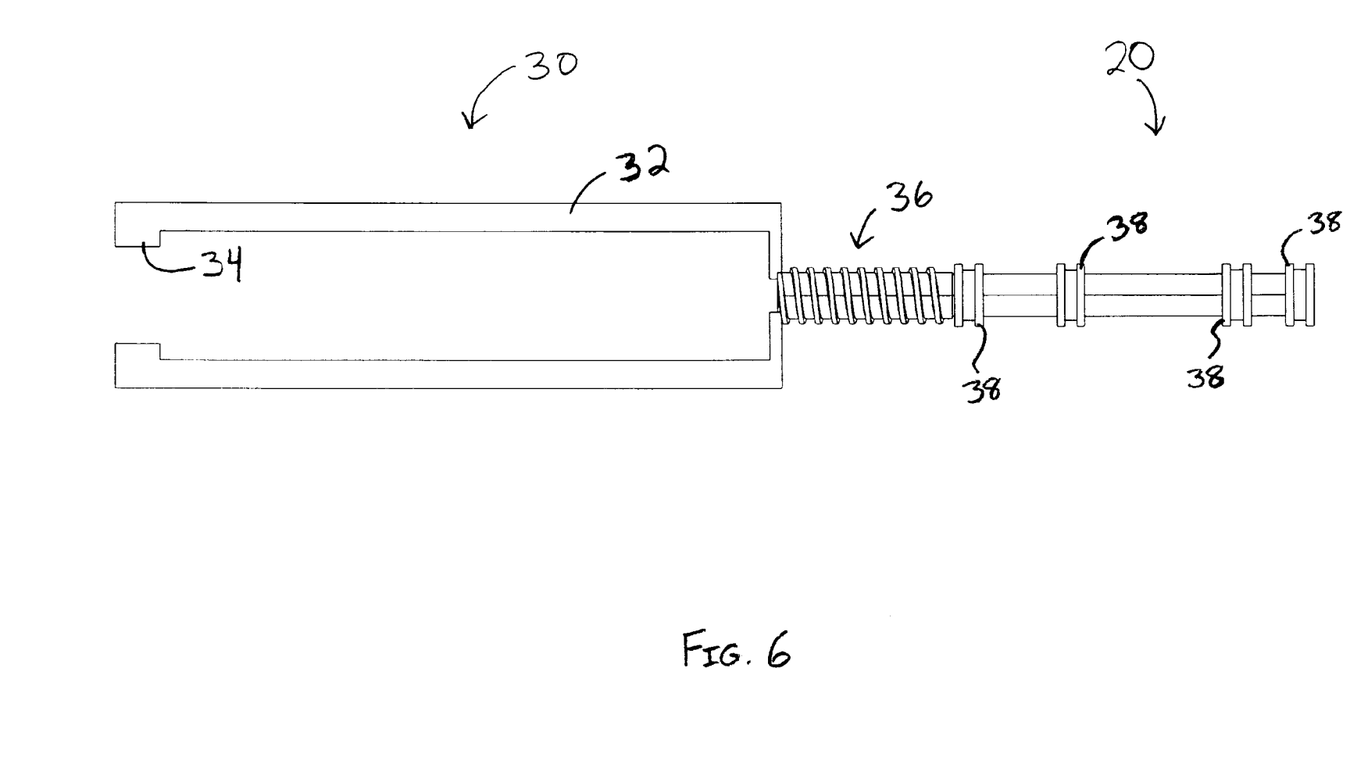
FIG. 6 depicts a plan view of an exemplary fork member of the biopsy device of FIG. 1.

As shown in FIG. 6, fork member (30) extends proximally from the valve member (20) of the present example. In particular, fork member (30) and valve member (20) are integrally formed together in this example. Accordingly, when valve member (20) translates longitudinally in this example, fork member (30) translates therewith. As shown, fork member (30) includes a pair of proximally extending arms (32), and the proximal end of each arm (32) has an inwardly directed prong (34). As will be described in greater detail below with reference to FIGS. 7-8, prongs (34) are configured to engage a flange (68) upon distal translation of fork member (30).

Fork member (30) further includes a threaded portion (36). A gear (40) is disposed about threaded portion (36). The longitudinal position of gear (40) within biopsy device (10) is substantially fixed in the present example, while gear (40) is configured to rotate within biopsy device (10). Gear (40) includes internal threads (not shown) that are configured to engage the external thread of threaded portion (36). In particular, as gear (40) rotates, the engagement of the threads causes fork member (30) to translate distally or proximally, depending upon the direction of rotation of gear (40). As noted above, such distal or proximal translation of fork member (30) may vary the relationship between valving member (20) and valve manifold (12), thereby varying fluid communication among ports (14, 16, 18) in the present example.

Figure 3:
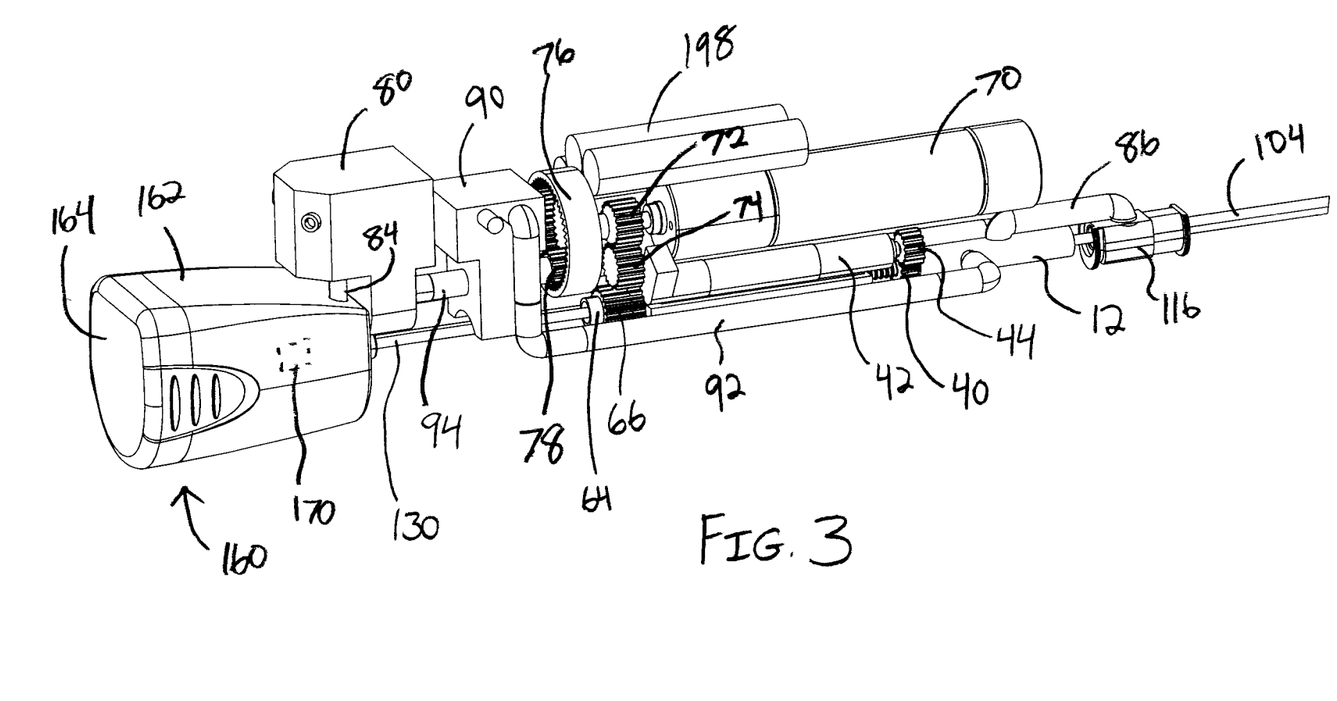
FIG. 3 depicts another partial perspective view of the biopsy device of FIG. 1 with housing components removed.

As shown in FIG. 3, a motor (42) with gear (44) is provided to rotate gear (40). In particular, motor (42) directly drives gear (44), which meshes with gear (40). Accordingly, fork member (30) may be translated distally or proximally, depending upon the direction in which motor (42) is activated to rotate. Of course, any other suitable components, configurations, or mechanisms, may be used to translate fork member (30) distally or proximally. By way of example only, in other embodiments, fork member (30) may be longitudinally driven pneumatically (e.g., by a pneumatic cylinder or actuator, etc.) or by a solenoid.

Figure 5:
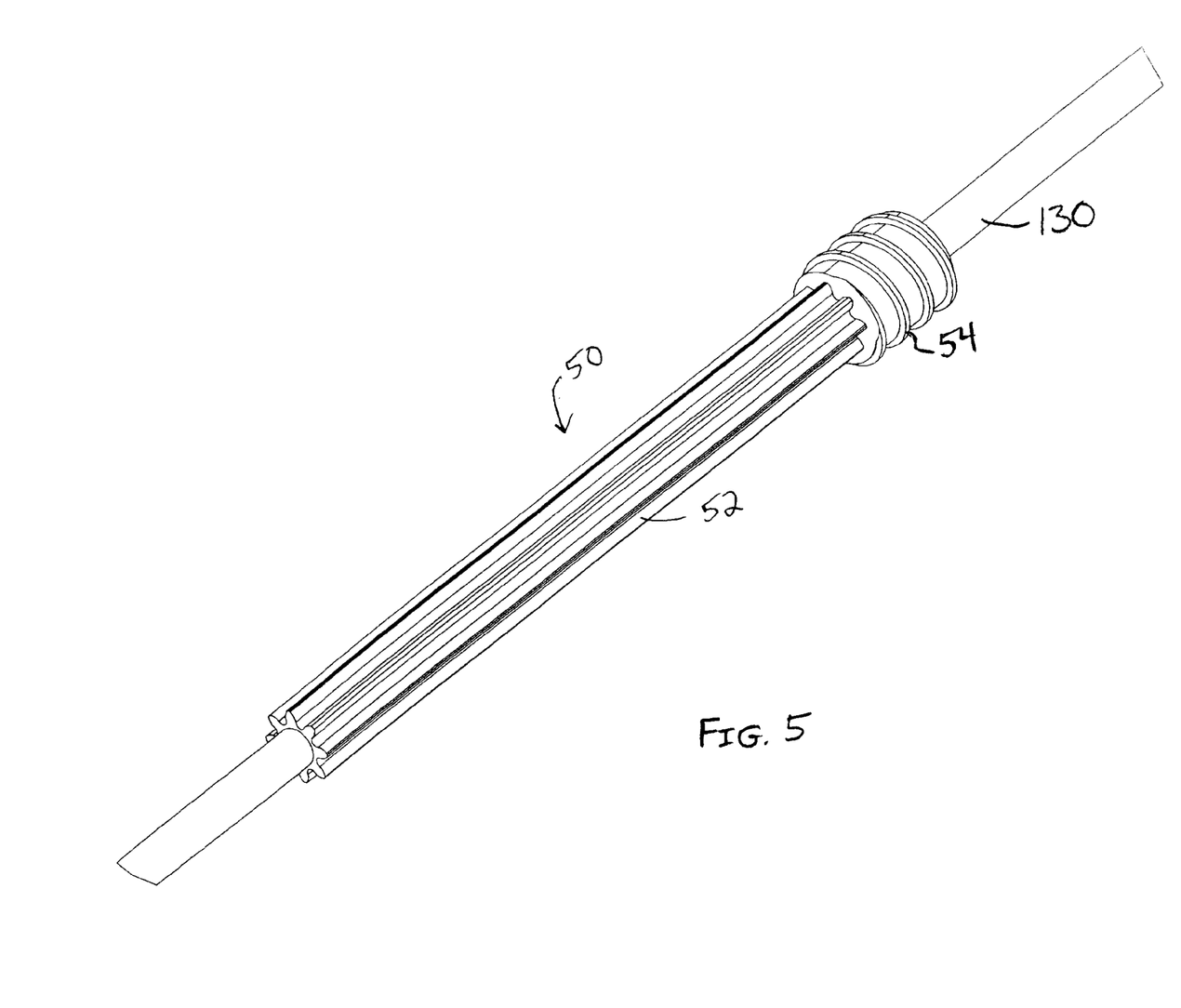
FIG. 5 depicts a perspective view of an exemplary cutter overmold of the biopsy device of FIG. 1.

In the present example, and as shown in FIG. 5, a cutter drive member (50) is provided about cutter (130). In particular, drive member (50) of the present example is overmolded about cutter (130) and is configured to rotate and translate unitarily therewith. In other versions, drive member (50) is secured relative to cutter (130) using other structures or techniques. Drive member (50) of the present example includes a splined portion (52) and a threaded portion (54).

As shown in FIGS. 2-3 and 7-8, a nut (60) is provided about drive member (50). Nut (60) is fixed within biopsy device (10), such that nut (60) is substantially prevented from rotating or translating within biopsy device (10). Nut (60) includes internal threads (not shown) that are configured to engage with the external thread on threaded portion (54) of cutter drive member (50). In particular, nut (60) and drive member (50) are configured such that cutter (130) will translate longitudinally relative to nut (60) (and relative to needle portion (102)) as drive member (50) is rotated, due to engagement of threads of nut (60) and threaded portion (54). The direction of longitudinal translation of cutter (130) depends on the direction of rotation of drive member (50) within nut (60) in this example. Drive member (50) may be rotated through engagement of splined portion (52), as will be described in greater detail below.

A drive gear (64) is provided about cutter (130) in the present example. Drive gear (64) includes a plurality of outer splines (66), an outwardly extending circumferential flange (68), and one or more internal splines (not shown). A spring (71) is provided between flange (68) of drive gear (64) and an outer flange (62) of nut (60). Spring (71) is configured to bias drive gear (64) proximally in this example. Of course any other type of resilient member or any other type of component in any other suitable location may be used to urge drive gear (64) proximally. While spring (71) of the present example is configured to bias flange (68) proximally against prongs (34) of fork member (30), even while fork member (30) is in a proximal position, spring (71) may alternatively have a shorter coiled length, such that flange (68) is not urged into contact with prongs (34) when fork member (30) is in a proximal position. Such a configuration of spring (71) may permit some proximal range of travel of fork member (30) without necessarily resulting in proximal motion of drive gear (64). Alternatively, spring (71) may bias drive gear (64) proximally against a feature in the housing (not shown), such that flange (68) is not urged into contact with prongs (34) when fork member (30) is in a proximal position. In such embodiments, suitable longitudinal gaps between flange (68) and prongs (34) when fork member (30) is in a proximal position will be apparent to those of ordinary skill in the art in view of the teachings herein.

As described above, and as illustrated in FIGS. 7-8, rotation of gear (40) by motor (42) may cause fork member (30) to translate distally or proximally, depending upon the direction of rotation of gear (40). With fork member (30) in a proximal position as shown in FIG. 7, drive gear (64) is positioned in its fully proximal position. When cutter (130) is advanced fully distal to "close off" aperture (108) and sever tissue that is prolapsed through aperture (108), splined portion (52) of cutter drive member (50) substantially disengages from drive gear (64), resulting in the termination of cutter (130) rotation and translation. In particular, the internal splines of drive gear (64) are no longer engaged with splined portion (52) of drive member (50). Thus, as drive gear (64) rotates when fork member (30) is in a proximal position, such rotation of drive gear (64) will not be imparted to cutter drive member (50) as the distal end of a cutter (130) reaches the distal end of the aperture (108). In other words, drive gear (64) will simply "freewheel" once the distal end of a cutter (130) reaches the distal end of the aperture (108) while fork member (30) is in a proximal position.

In the present example, when gear (40) is rotated by motor (42) to translate fork member (30) to a distal position, as shown in FIG. 8, such distal translation of fork member (30) will result in distal movement of drive gear (64). In particular, prongs (34) engaged with flange (68) will pull drive gear (64) distally. Such distal movement of drive gear (64) will cause the internal spline(s) of drive gear (64) to engage with splined portion (52) of cutter drive member (50). Upon such engagement, rotation of drive gear (64) will cause concomitant rotation of drive member (50). As described above, due to engagement of threaded portion (54) of drive member (50) with internal threads of nut (60), such rotation of drive member (50) will cause distal or proximal translation of cutter (130), depending on the direction of rotation.

In view of the above, it will be appreciated that drive gear (64), drive member (50), and nut (60) are configured to provide simultaneous rotation and translation of cutter (130). It will also be appreciated in view of the teachings herein that fork member (30) is configured to provide both clutching and valving functions. In particular, fork member (30) is configured to serve as a clutch by selectively engaging drive gear (64) with cutter drive member (50); while also providing valving by repositioning seals (38) of valving member (20) relative to ports (14, 16, 18) of valve manifold (12).

In some embodiments, however, valving member (20) is configured such that fork member (30) may translate through certain longitudinal ranges without affecting the pneumatic level of vacuum lumen (114). For instance, valving member (20) may be configured such that a longitudinal range of travel of fork member (30) that includes a longitudinal position just prior to and during initial stages of engagement between drive gear (64) and cutter drive member (50) has no appreciable effect on the pneumatic level of vacuum lumen (114). Exemplary pneumatic algorithms that may be provided by valving member (20) and valve manifold (12) will be described in greater detail below with reference to FIG. 9.

In the present example, a second motor (70) is provided for rotating drive gear (64). In particular, a first gear (72) is provided on the shaft extending from motor (70). An intermediary gear (74) is positioned between and engaged with first gear (72) and drive gear (64). Accordingly, rotation of motor (70) is communicated to drive gear (64) via meshing gears (72, 74). Of course, any other suitable structures or techniques may be used to drive a drive gear (64) (e.g., belt, chain, etc.). In the present example, splines (66) of drive gear (64) have a sufficient length such that they remain meshed with splines of intermediary gear (74) both when drive gear (64) is in a proximal position (e.g., disengaged from cutter drive member (50) while cutter (130) is advanced fully distal) and when drive gear (64) is in a distal position (e.g., engaged with cutter drive member (50)).

Figure 2:
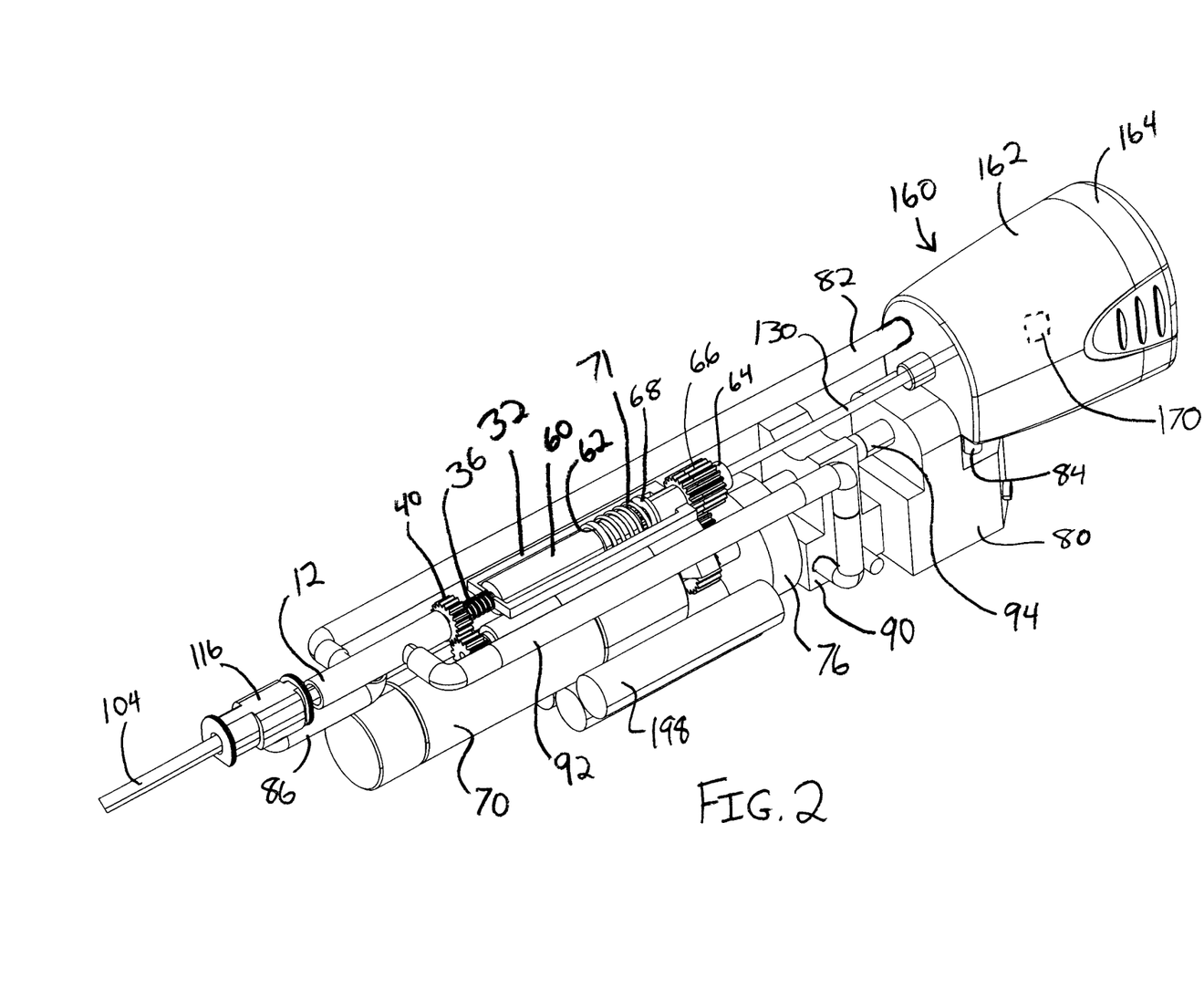
FIG. 2 depicts a partial perspective view of the biopsy device of FIG. 1 with housing components removed.

Biopsy device (10) of the present example also includes a pressure pump (90). As shown in FIGS. 2-3, a ring gear (76) is provided on the shaft extending from motor (70). Ring gear (76) is engaged with a gear (78) extending from pressure pump (90). Pressure pump (90) is configured to pressurize air in response to rotation of gear (78). Suitable internal configurations for pressure pump (90) to pressurize air in response to rotation of gear (78) will be apparent to those of ordinary skill in the art in view of the teachings herein.

As noted above, a conduit (92) is fluidly coupled with pressure pump (90). In particular, conduit (92) is configured to communicate pressurized air from pressure pump (90). As also noted above, conduit (92) is fluidly coupled with port (16) of valve manifold (12), such that pressurized air from pressure pump (90) may be selectively communicated to vacuum lumen (114) of needle portion (102), depending on the longitudinal position of valving member (20) within valve manifold (12). In other words, pressure pump (90) may be used to communicate pressurized air to vacuum lumen (114) in the present example.

Of course, air or some other medium may be pressurized using a variety of alternative structures, devices, and techniques, and a pressurized medium may be communicated along a variety of alternative paths using any suitable structures, devices, and techniques.

In the present example, pressure pump (90) is coupled with vacuum pump (80) via a coupling (94). In some embodiments, coupling (94) comprises one or more torque transfer components, such as a rotating shaft (not shown) and/or other structure(s). For instance, coupling (94) may include a component that is in mechanical communication with gear (78), such that rotation imparted by motor (70) may be communicated via coupling (94). Suitable internal configurations that may be provided within pressure pump (90) to provide such communication to coupling (94) will be apparent to those of ordinary skill in the art in view of the teachings herein. Pressure pump (90) may also be configured to provide rotary actuation through coupling (94) as a function of pressure within pressure pump (90). For instance, pressure pump (90) may include an impeller or other structure that rotates in response to pressurized air. In this example of rotary actuation or torque communication via coupling (94), vacuum pump (80) is configured to create a vacuum in response to rotary actuation through coupling (94). Suitable internal configurations for vacuum pump (80) to create a vacuum in response to rotary actuation through coupling (94) will be apparent to those of ordinary skill in the art in view of the teachings herein.

In other variations, coupling (94) provides fluid communication to vacuum pump (80). For instance, coupling (94) may provide a sealed fluid passage from pressure pump (90) to vacuum pump (80). Pressurized air generated by pressure pump (90) may thus be communicated to vacuum pump (80), thereby driving vacuum pump (80) to create a vacuum. Suitable internal structures and configurations for vacuum pump (80) to create a vacuum in response to receiving pressurized air will be apparent to those of ordinary skill in the art in view of the teachings herein.

Vacuum pump (80) of the present example is in fluid communication with the interior of tissue sample holder (160) via a port (84). Conduit (82) is also in communication with the interior of tissue sample holder (160). Tissue sample holder (160) is thus configured such that a vacuum communicated to tissue sample holder (160) by vacuum pump (80) via port (84) will be further communicated to vacuum conduit (82). As described above, a vacuum communicated to vacuum conduit (82) may further be communicated to vacuum lumen (114), depending on the longitudinal position of valving member (20) within valve manifold (12).

In the present example, cutter lumen (132) is also in fluid communication with the interior of tissue sample holder (160). Accordingly, a vacuum created within tissue sample holder (160) by vacuum pump (80) via port (84) is communicated to cutter lumen (132) in addition to being communicated to conduit (82). Such a vacuum in cutter lumen (132) may be sufficient to draw a tissue sample (that has been severed by cutter (130)), proximally into tissue sample holder (160). Proximal communication of tissue samples through cutter lumen (132) may be further assisted by pressurized air generated by pressure pump (90), which may be communicated through the distal end of cutter lumen (132) via vacuum lumen (114) (as described above) and openings between vacuum lumen (114) and cannula lumen (110). In other words, pressurized air generated by pressure pump (90) may impinge against the distal face of severed tissue samples within cutter lumen (132), assisting the proximal movement of such tissue samples toward and into tissue sample holder (160).

Of course, a vacuum may alternatively be created using a variety of alternative structures, devices, and techniques, and may be communicated along a variety of alternative paths using any suitable structures, devices, and techniques.

While the present example includes pumps (80, 90) for providing a vacuum and pressure to ports (14, 16) of valve manifold (12), respectively, it will be appreciated in view of the teachings herein that valve manifold (12) may include one or more additional ports (not shown), such as for receiving atmospheric air (e.g., for venting), saline (e.g., for flushing), or some other fluid. Suitable ways in which atmospheric air, saline, and/or other fluids may be incorporated into pneumatic algorithms for biopsy device (10) will be apparent to those of ordinary skill in the art in view of the teachings herein. By way of example only, some such algorithms are disclosed in U.S. Non-Provisional patent application Ser. No. 11/942,764, filed Nov. 20, 2007, entitled "Vacuum Timing Algorithm for Biopsy Device," the disclosure of which is incorporated by reference herein in its entirety.

In some embodiments, a vacuum sensor (170) is provided within tissue sample holder (160). Vacuum sensor (170) is configured to sense the level of vacuum within tissue sample holder (160). In particular, vacuum sensor (170) may be used to sense the vacuum level as a function of the longitudinal position of cutter (130). By way of example only, if vacuum sensor (170) indicates that the vacuum level within tissue sample holder (160) has not fallen below a predefined level (which may indicate that a tissue sample is lodged in aperture (108) and/or cutter lumen (132)), a "clear probe" algorithm may be initiated as described below.

It will be appreciated in view of the teachings herein that a variety of types of devices and configurations may be used to provide a vacuum sensor (170). For instance, vacuum sensor (170) may comprise a diaphragm, a capacitive coupling, a strain gauge, or any other suitable device(s), component(s), or configurations.

In addition, while vacuum sensor (170) is located within tissue sample holder (160) in the present example, it will be appreciated that vacuum sensor (170) may be positioned at any suitable location within tissue sample holder (160) or elsewhere within biopsy device (10). By way of example only, vacuum sensor (170) may be located within vacuum pump (80), within port (84), within cutter lumen (130), or elsewhere. The predefined vacuum level (which may indicate that a tissue sample is lodged in aperture (108) and/or in cutter lumen (132)) may need to be adjusted based on the location of the vacuum sensor (170) and/or based on other factors. In the present example, however, vacuum sensor (170) is positioned such that it can detect the level of vacuum within cutter lumen (132). Furthermore, more than one vacuum sensor (170) may be provided. Alternatively, vacuum sensor (170) may be omitted altogether.

In addition to or in lieu of a vacuum sensor (170), biopsy device (10) may also include a pressure sensor (not shown). Such a pressure sensor may be provided in any suitable location, including but not limited to within pressure pump (90), within conduit (92), within valve manifold (12), or elsewhere. A pressure sensor may be configured similar to a vacuum sensor (170) (e.g., including a diaphragm, a capacitive coupling, a strain gauge, or any other suitable device(s), component(s), or configurations), or may be otherwise configured. A pressure sensor may be used to sense pressure generated by pressure pump (90). Such pressure data may be communicated and used in a variety of ways, including but not limited to techniques described in further detail below. As with vacuum sensor (170) and various other components described herein, a pressure sensor is merely optional, and may be omitted altogether.

Regardless of whether one or both of a vacuum sensor (170) or pressure sensor are used, signals or data communicated from such sensor(s) may be processed using any suitable components. By way of example only, one or both of a vacuum sensor (170) or pressure sensor may be communicatively coupled with an ASIC, a microcontroller, and/or some other component, which may be in further communication with either or both motors (42, 70), and which may be located within biopsy device (10) or elsewhere. Such a controller (not shown) may provide a variety of responses as a function of a variety of conditions.

For instance, where biopsy device (10) includes a vacuum sensor (170), a controller may initiate a "clear probe" cycle, such as when vacuum sensor (170) detects that the vacuum level within cutter lumen (132) has not fallen below a certain level when it should be below that level. In particular, a range of vacuum levels within cutter lumen (132) may indicate that a tissue sample is lodged within cutter lumen (132) and/or within aperture (108). In response to such a condition, a "clear probe" cycle may begin with cutter (130) being advanced to close aperture (108), to the extent that aperture (108) is not already closed. Alternatively, cutter (130) may be positioned such that aperture (108) is opened just slightly. In either case, pressure may be communicated to vacuum lumen (114), and vacuum communicated to cutter lumen (132). As described above, pressure communicated to vacuum lumen (114) may cross into cannula lumen (110) via openings in wall (120), thereby impinging against the distal face of tissue that is lodged within cutter lumen (132). Cutter (130) may be reciprocated (e.g., to alternate between closing off, and slightly opening, aperture (108)) one or more times at this stage. Such a process may continue until vacuum sensor (170) indicates that a satisfactory level of vacuum has once again been obtained. Other ways in which a "clear probe" cycle may be carried out will be apparent to those of ordinary skill in the art in view of the teachings herein.

In addition to or in lieu of initiating a "clear probe" cycle as described above in response to certain conditions, such sensor(s) and other components may provide a variety of other types of responses under certain conditions. For instance, biopsy device (10) may be configured such that cutter (130) will not translate longitudinally until pumps (80, 90) have generated a sufficient amount of vacuum and/or pressure, respectively. Suitable threshold levels of vacuum and/or pressure will be apparent to those of ordinary skill in the art in view of the teachings herein.

A controller may also obtain data from one or more sensors at any suitable time and/or rate. For instance, when motors (42, 70) have been activated at initial stages of use of a biopsy device (10), one or more sensors may be polled to check biopsy device (10) for fluid leaks. If a leak is detected, the controller may prevent further use of biopsy device (10), and may further provide an indication to the user (e.g., illuminating a "trouble light," etc.). Of course, a controller may also provide an indication to the user when other conditions are detected (e.g., tissue sample stuck in aperture (108) or cutter lumen (132)). Other ways in which sensors may be used with a biopsy device (10) will be apparent to those of ordinary skill in the art in view of the teachings herein.

It will be appreciated in view of the teachings herein that motor (70) may continue to drive or charge pressure pump (90) and/or vacuum pump (80), even while drive gear (64) is disengaged from cutter drive member (50). For instance, such "idle" charging of pressure pump (90) and/or vacuum pump (80) may be desirable when multiple tissue samples are being taken during a single insertion of needle portion (102) within a patient. In other words, a user may wait to let motor (70) charge pressure pump (90) and/or vacuum pump (80) between sampling cycles, even while needle portion (102) remains inserted within a patient. During this time, the cutter (130) may be advanced distally, "closing off" aperture (108), and the user may reposition biopsy device (10) (e.g., by rotating needle portion (102) within patient to re-orient aperture (108)).

In view of the above, it will be appreciated that a first motor (42) may be used to selectively translate fork member (30) distally or proximally, depending on the direction of rotation of motor (42), in order to provide simultaneous clutching and valving functions (among other potential functions). It will also be appreciated that a second motor (70) may be used to simultaneously drive a drive gear (64), a pressure pump (90), and a vacuum pump (80). Those of ordinary skill in the art will appreciate in view of the teachings herein, however, that a single motor may be used to serve all such functions and/or other functions. For instance, one or more clutches may be added to selectively engage a variety of gears or other components with one or more drive shafts or drive gears. In addition, while motors (42, 70) of the present example are electrical, driven by batteries (198), motors (42, 70) may alternatively comprise one or more pneumatic motors, pneumatic actuators, or other devices.

To the extent that batteries (198) are used, such batteries may be rechargeable or non-rechargeable. In some alternate embodiments, biopsy device (10) receives power via wires from an external power source. In other embodiments, biopsy device (10) receives power from a separate source wirelessly. In still other embodiments, biopsy device (10) receives power from a source of pressurized medium (e.g., an on-board manual pump, a separate pump connected to biopsy device (10) via a conduit, etc.). It will also be apparent to those of ordinary skill in the art in view of the teachings herein that biopsy device (10) of the present example is tetherless, such that no wires, conduits, tubes, or other components need to be connected to biopsy device (10) in order for it to function fully. In other words, biopsy device (10) is substantially portable, and may be used in a variety of settings. Of course, other variations of biopsy device (10) may include one or more tethers, such as a wire, cable, tube, etc. In addition, motors (42, 70), batteries (198), pressure pump (90), and vacuum pump (80) in the present example are located within re-usable holster (200) of biopsy device (10). However, other variations may include any or all such components in disposable probe (100) or elsewhere. Still other suitable components and arrangements of components for variations of biopsy device (10) will be apparent to those of ordinary skill in the art in view of the teachings herein.

Figure 9:
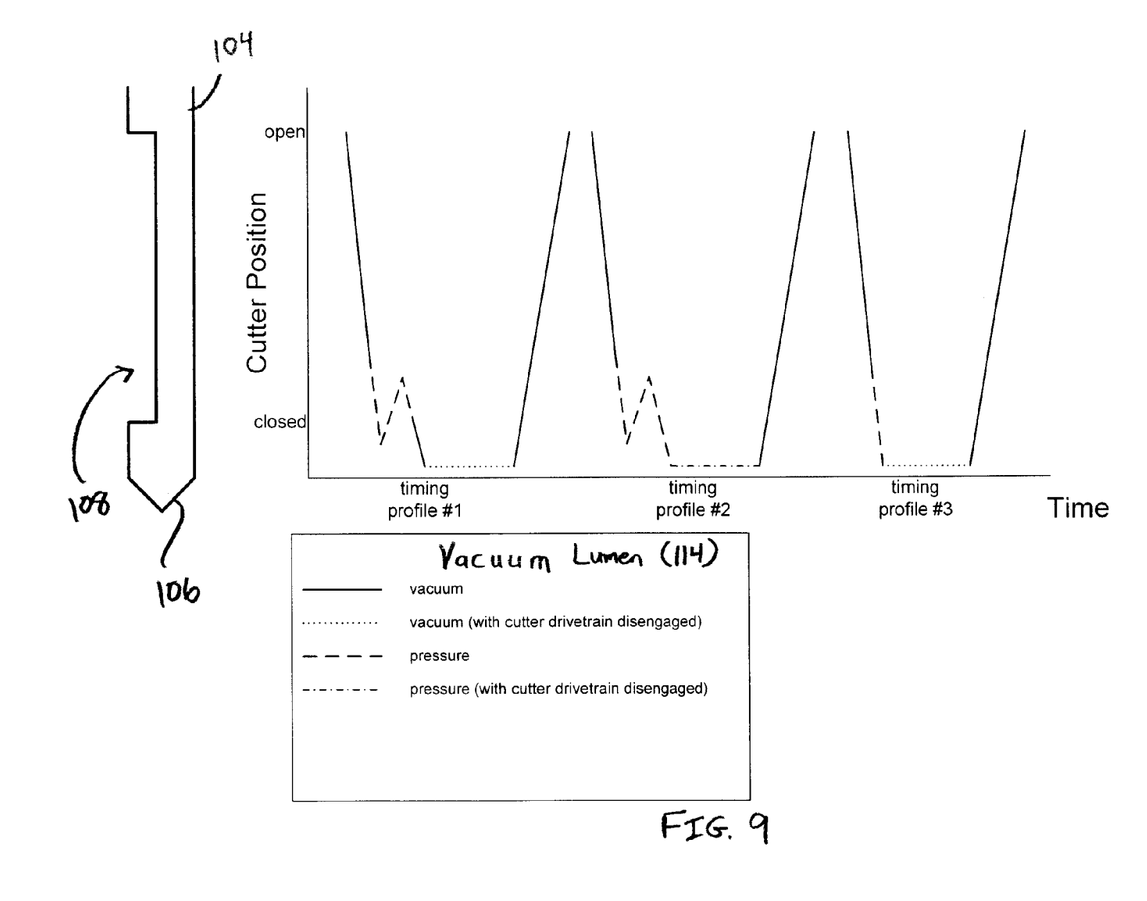
FIG. 9 depicts an exemplary timing algorithm that may be used for providing fluid communication to a vacuum lumen as a function of cutter position.

FIG. 9 depicts examples of how fluid may be communicated to vacuum lumen (114) as a function of both the longitudinal position of cutter (130) and time. Such pneumatic algorithms may be provided by selective motor (42) activation, which may be used to selectively vary the longitudinal position of valve member (20) within valve manifold (12). Of course, variation of the longitudinal position of cutter (130) may be provided by selective motor (70) activation in conjunction with clutching by fork member (30) as described above. As shown, the pneumatic algorithms begin with the cutter (130) being retracted proximally, such that aperture (108) is "open." It will be appreciated, however, that cutter (130) may actually be advanced distally to "close" aperture (108) when needle portion (102) is inserted into a patient's breast. In other words, the cutter (130) may be retracted proximally, and the illustrated pneumatic algorithms initiated, after needle portion (102) has been inserted into a patient's breast.

In the present example, a vacuum is communicated to vacuum lumen (114) before cutter (130) begins translating distally, thereby drawing or prolapsing tissue into aperture (108). As shown, a vacuum may continue to be communicated to vacuum lumen (114) via port (14) as cutter (130) moves toward a distal position, retaining tissue drawn into aperture (108). During this time, port (16) may be essentially sealed (a.k.a. "dead-headed") by valving member (20), such that pressurized air from pressure pump (90) is not communicated past seals (38) or otherwise to vacuum lumen (114). This may be accomplished by advancing valving member (20) to a distal position, such as is shown in FIG. 8.

As cutter (130) approaches a distal position, pressurized air may be communicated to vacuum lumen (114), during which time cutter (130) is severing tissue. While pressurized air is communicated to vacuum lumen (114), port (14) may be essentially sealed (a.k.a. "dead-headed") by valving member (20), such that vacuum from vacuum pump (80) is not communicated past seals (38) or otherwise to vacuum lumen (114). This may be accomplished by retracting valving member (20) to a proximal position, such as is shown in FIG. 7. Cutter (130) may reciprocate one or more times near the distal edge of aperture (108) with pressurized air continuing to be provided to vacuum lumen (114). It will be appreciated that spring (71) may be configured to permit drive gear (64) to provide reciprocation of cutter (130), even while valving member (20) and fork member (30) are in a proximal position.

Cutter (130) may then be advanced distally to a degree sufficient to "close off" aperture (108). At this point, cutter (130) will have severed a tissue sample from tissue that had been prolapsed through aperture (108) in the present example. Concurrently, drive gear (64) disengages from drive ember (50), leaving cutter (130) in a distal position and no longer rotating or translating. While cutter (130) is in a distal position, vacuum may again be communicated through vacuum lumen (114), as shown in FIG. 9. Alternatively, as also shown in FIG. 9, pressurized air may be communicated through vacuum lumen while cutter (130) is in a distal position. Such pressurized air may be communicated to vacuum lumen (114) either with drive gear (64) engaging cutter drive member (50) or without drive gear (64) engaging cutter drive member (50).

Regardless of whether vacuum or pressure is communicated through vacuum lumen (114) at this stage, a vacuum communicated through cutter lumen (132) may draw a tissue sample severed by cutter (130) proximally into tissue sample holder (160). Of course, to the extent that pressurized air or other pressurized fluid is being communicated to vacuum lumen (114), such a pressurized medium may assist the axial vacuum through cutter lumen (132) to drive a tissue sample proximally through cutter lumen (132) and into tissue sample holder (160).

To the extent that drive gear (64) has been disengaged from drive member (50) at this point, drive gear (64) may then be re-engaged with drive member (50), rotating in a different direction to translate cutter (130) proximally. A vacuum may again be communicated to vacuum lumen (114) as cutter (130) is retracted, thereby drawing additional tissue into aperture (108) for subsequent sampling. The process may be repeated until a desired number of tissue samples are obtained. Vacuum may be communicated through cutter lumen (132) throughout the entire process, or otherwise.

As is also shown in FIG. 9, reciprocation of cutter (130) during a sampling cycle is merely optional. In other words, a cutter (130) may simply travel distally to sever a tissue sample in one motion, then remain in a distal position while the tissue sample travels proximally through cutter lumen (132) (and while vacuum pump (80) recharges and/or pressure pump (90) recharges, etc.), then travel proximally to permit a subsequent tissue sample to be taken. Other ways in which cutter (130) motion may be provided, as well as ways in which pneumatic communication may be provided to vacuum lumen (114) and/or cutter lumen (132) as a function of cutter position (130) or otherwise, will be apparent to those of ordinary skill in the art in view of the teachings herein.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed an sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A biopsy device comprising:
   (a) a handpiece;
   (b) a hollow cutter translatable relative to the handpiece and operable to sever tissue samples;
   (c) a vacuum source for providing vacuum within the hollow cutter;
   (d) a tissue sample receiving member associated with the handpiece and positioned for receiving tissue samples transported through the hollow cutter;
   (e) a vacuum sensor disposed within the handpiece and positioned to measure levels of vacuum in the tissue sample receiving member, wherein the vacuum sensor is configured to measure the levels of vacuum for a predetermined amount of time to take a plurality of vacuum level measurements as a function of a longitudinal position of the cutter; and
   (f) a controller, wherein the controller is communicatively coupled to the vacuum sensor, wherein the controller is operable to regulate the translation of the hollow cutter, wherein the controller is further operable to translate the hollow cutter through a predetermined operational cycle when the at least one of the plurality of vacuum level measurements fall within a predetermined range.

2. The biopsy device of claim 1 further comprises a motor communicatively coupled to the controller, wherein the controller is operable to regulate the speed of the motor.

3. The biopsy device of claim 1 wherein the controller is operable to regulate the level of vacuum produced by the vacuum source.

4. The biopsy device of claim 1 further comprising a valving member located within the handpiece, wherein the controller is operable to regulate the position of the valving member.

5. The biopsy device of claim 4 wherein the valving member is positioned within a manifold, wherein at least a portion of the manifold is in communication with the vacuum source.

6. The biopsy device of claim 1 wherein the controller is configured to respond to an indication from the vacuum sensor that the level of vacuum is below a predetermined level of vacuum.

7. The biopsy device of claim 1 wherein the controller is configured to respond to an indication from the vacuum sensor that the level of vacuum is above a predetermined level of vacuum and that the predetermined amount of time to take the plurality of vacuum level measurements as the function of the longitudinal position of the cutter has elapsed.

8. The biopsy device of claim 1 wherein the vacuum sensor is coupled to the vacuum source.

9. A biopsy device comprising:
   (a) a handpiece;
   (b) a hollow cutter translatable relative to the handpiece and operable to sever tissue samples;
   (c) a pressure pump in fluid communication with the hollow cutter;
   (d) a tissue sample receiving member associated with the handpiece and positioned for receiving tissue samples transported through the hollow cutter;
   (e) a controller; and
   (f) a pressure sensor disposed within the handpiece, and wherein the pressure sensor is in fluid communication with the tissue sample receiving member to detect a level of pressure in the hollow cutter, wherein the pressure sensor is further operable to communicate the level of pressure to the controller, wherein the controller is configured to respond to the level of pressure communicated from the pressure sensor to initiate a predetermined operational cycle when the level of pressure is below a predetermined clear probe level of pressure.

10. The biopsy device of claim 9 further comprising a valving mechanism comprising a valving member and a manifold, wherein the valving mechanism is located within the handpiece, wherein the valving member is disposed within the manifold, and wherein the controller is operable to regulate movement of the valving member.

11. The biopsy device of claim 9 wherein the controller is operable to regulate the translation of the hollow cutter.

12. A method for clearing tissue from within a biopsy device, wherein the biopsy device comprises a handpiece, a probe extending distally from the handpiece, and a tissue sample holder configured to receive severed tissue from the probe, wherein the handpiece comprises a sensor operable to measure levels of vacuum in the tissue sample holder, a motor, and a controller, wherein the probe comprises a needle and a hollow cutter disposed within the needle, wherein the motor is operable to translate the hollow cutter, and wherein the controller is communicatively coupled to the sensor and operable to regulate the motor, the method comprising the steps of:
  (a) receiving a signal from the sensor indicative of the measured levels of vacuum in the tissue sample holder;
  (b) monitoring the signal from the sensor for a predetermined period of time to store the measured levels of vacuum as a function of the longitudinal position of the cutter using the controller, wherein the measured levels of vacuum monitored during the predetermined period of time are stored as a first set of measured levels of vacuum;
  (c) determining if the first set of measured levels of vacuum have decreased below a predetermined level of vacuum after the predetermined period of time since the signal was monitored by using the controller to compare the first set of measured levels of vacuum to the predetermined level of vacuum; and
  (d) translating the cutter one or more times in response to the determination that the first set of measured levels of vacuum have decreased below the predetermined level of vacuum.

13. The method of claim 12 further comprising the step of repeating the translation of the cutter until the measured levels of vacuum have decreased below the predetermined level of vacuum.

* * * * *